US00PP29892P3

(12) United States Plant Patent
Pineau

(10) Patent No.: US PP29,892 P3
(45) Date of Patent: Nov. 27, 2018

(54) ***PHYSOCARPUS* PLANT NAMED 'MINALL2'**

(50) Latin Name: *Physocarpus opulifolius*
Varietal Denomination: Minall2

(71) Applicant: Hortival Diffusion SAS, Beaufort-en-Anjou (FR)

(72) Inventor: Patrick Pineau, Saint-Mathurin-sur-Loire (FR)

(73) Assignee: Hortival Diffusion SAS, Beaufort-en-Anjou (FR)

( * ) Notice: Subject to any disclaimer, the term of this patent is extended or adjusted under 35 U.S.C. 154(b) by 0 days.

(21) Appl. No.: 15/530,088

(22) Filed: Dec. 1, 2016

(65) Prior Publication Data

US 2017/0181348 P1 Jun. 22, 2017

Related U.S. Application Data

(60) Provisional application No. 62/386,951, filed on Dec. 16, 2015.

(51) Int. Cl.
*A01H 5/00* (2018.01)

(52) U.S. Cl.
USPC ..... Plt./226
CPC ..... *A01H 5/00* (2013.01)

(58) Field of Classification Search
USPC ..... Plt./226
CPC ..... A01H 5/00
See application file for complete search history.

(56) References Cited

PUBLICATIONS

GTITM UPOVROM Plant Variety Database Citation of 'Minall2' as per QZ PBR 20141502; Jun. 2, 2014.*

* cited by examiner

*Primary Examiner* — Kent L Bell
(74) *Attorney, Agent, or Firm* — Audrey Charles

(57) ABSTRACT

A new and distinct cultivar of *Physocarpus* plant named 'Minall2', characterized by its bright red-colored immature foliage, dark purple-colored mature foliage, and moderately vigorous, compact-upright growth habit, is disclosed.

2 Drawing Sheets

Latin name of genus and species of plant claimed: *Physocarpus opulifolius*.

Variety denomination: 'Minall2'.

BACKGROUND OF THE INVENTION

The present invention relates to a new and distinct cultivar of *Physocarpus* plant botanically known as *Physocarpus opulifolius* and hereinafter referred to by the cultivar name 'Minall2'.

The new cultivar originated in a controlled breeding program in La Menitre, Maine et Loire, France during May 2008. The objective of the breeding program was the development of *Physocarpus* cultivars with dark purple-colored foliage and a compact growth habit.

The new *Physocarpus* cultivar was the result of cross-pollination. The female (seed) parent of the new cultivar is the proprietary breeding selection coded 11078, not patented, characterized by its white-colored flowers, medium purple-colored foliage, and moderately vigorous, upright growth habit. The male (pollen) parent of the new cultivar is COPPERTINA 'Mindia', U.S. Plant Pat. No. 16,317, characterized by its white-colored flowers, medium copper-colored foliage, and vigorous, upright-mounding growth habit. The new cultivar was discovered and selected as a single flowering plant within the progeny of the above stated cross-pollination during August 2011 in a controlled environment in La Menitre, Maine et Loire, France.

Asexual reproduction of the new cultivar by terminal stem cuttings since August 2011 in La Menitre, Maine et Loire, France, and Mt. Angel, Oreg. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Minall2' as a new and distinct cultivar of *Physocarpus* plant:

1. Bright red-colored immature foliage;
2. Dark purple-colored mature foliage; and
3. Moderately vigorous, compact-upright growth habit.

Plants of the new cultivar differ from plants of the female and male parents primarily in having darker purple foliage and a more compact growth habit.

Of the many commercially available *Physocarpus* cultivars, the most similar in comparison to the new cultivar is 'Seward', U.S. Plant Pat. No. 14,821. However, in side-by-side comparisons, plants of the new cultivar differ from plants of 'Seward' in at least the following characteristics:

1. Plants of the new cultivar are shorter than plants of 'Seward';
2. Plants of the new cultivar are better branched than plants of 'Seward';
3. Plants of the new cultivar have brighter red-colored immature foliage than plants of 'Seward'; and
4. Plants of the new cultivar have darker purple-colored mature foliage than plants of 'Seward'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Minall2'. The plants were approximately two-years old and grown in three-gallon containers for approximately one year in West Grove, Pa. Flower photos were taken from a five-year old plant gown in Beaufort en Vallée, Maine et Loire, France. The plant was grown outdoors in a ten-liter container and then transplanted and grown in the ground for approximately five months.

DETAILED BOTANICAL DESCRIPTION

Figure 1:
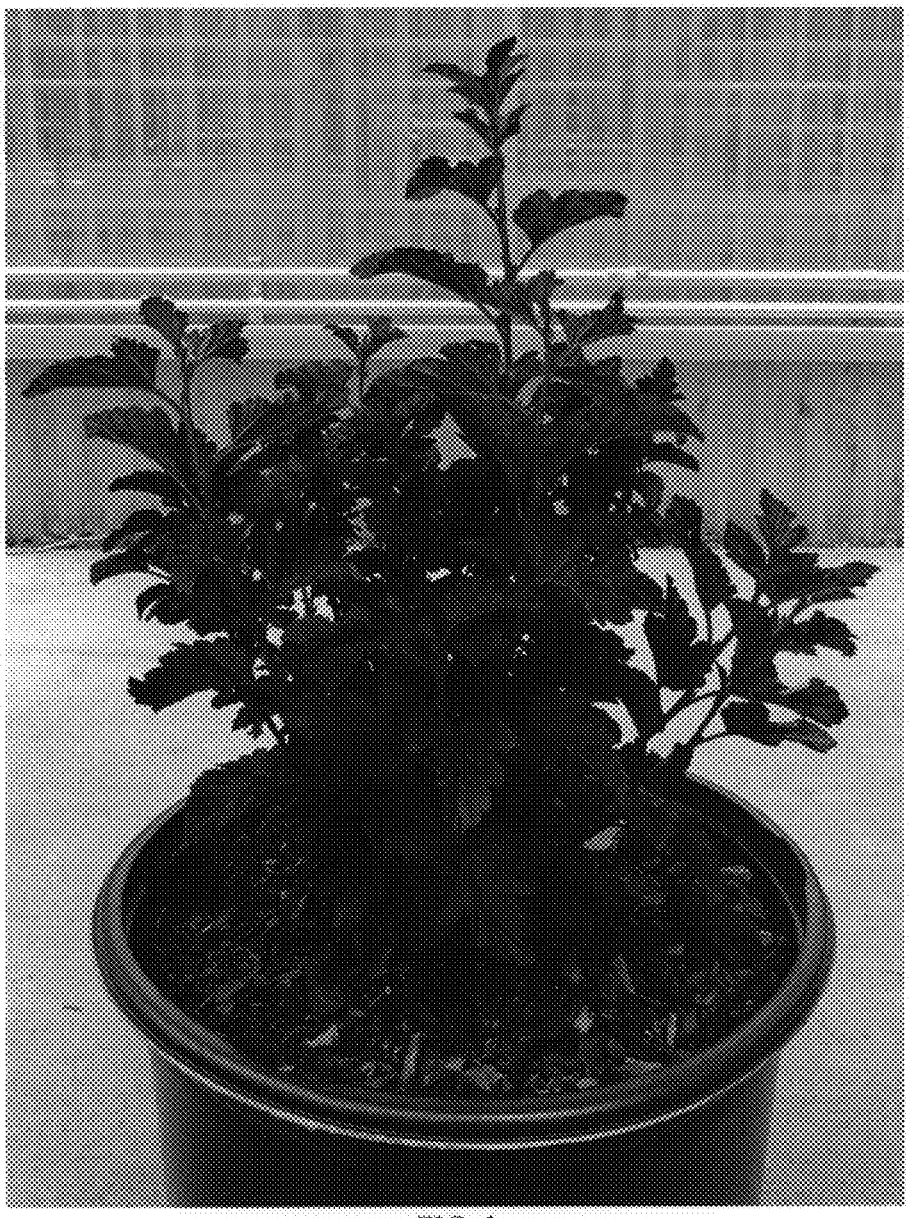
FIG. 1 illustrates a side view of the overall growth and habit of 'Minall2'.
Figure 2:
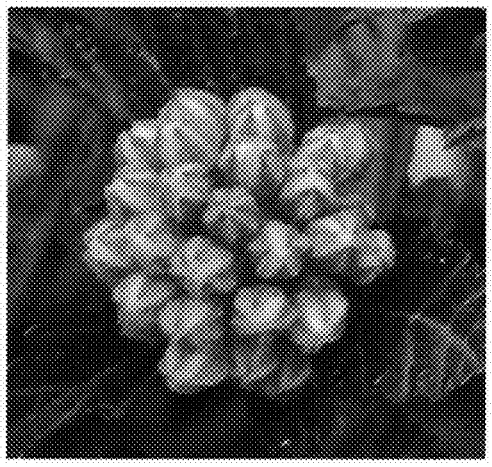
FIG. 2 illustrates a close-up view of an immature individual inflorescence of 'Minall2'.
Figure 3:
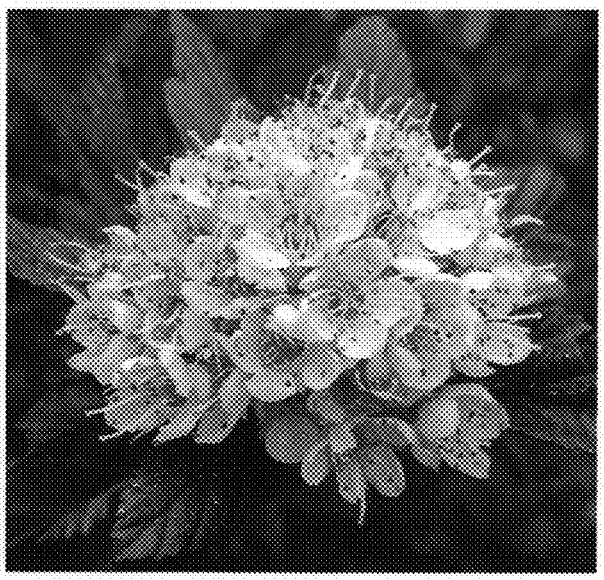
FIG. 3 illustrates a close-up view of a mature individual inflorescence of 'Minall2'.

For general plant characteristics the chart used in the identification of colors described herein is The R.H.S. Colour Chart of The Royal Horticultural Society, London, England, 2015 edition, except where general color terms of ordinary significance are used. The color values were determined in August 2016 under natural light conditions in West Grove, Pa. For flower characteristics the chart used in the identification of colors described herein is The R.H.S. Colour Chart of The Royal Horticultural Society, London, England, 2011 edition. The color values were determined in May 2018 under natural light conditions in Beaufort en Vallée, Maine et Loire, France.

For general plant characteristics, the following descriptions and measurements describe approximately two-year old plants produced from cuttings from stock plants and grown under conditions comparable to those used in commercial practice. The plants were grown in West Grove, Pa. for approximately one year in three-gallon containers utilizing a soilless growth medium. Plants were maintained in a greenhouse during winter months and grown outdoors for the remainder of the year. For flowering characteristics, the descriptions and measurements describe flowers from five-year old plants gown in Beaufort en Vallée, Maine et Loire, France. The plants were grown in ten-liter containers and then transplanted in the ground and grown for approximately five months. Measurements and numerical values represent averages of typical plants.

Botanical classification: *Physocarpus opulifolius* cultivar Minall2.

Parentage:

*Female parent.*—Proprietary breeding selection coded 11078, not patented.

*Male parent.*—COPPERTINA 'Mindia', U.S. Plant Pat. No. 16,317.

Propagation:

*Type cutting.*—Softwood.

*Time to initiate roots.*—Approximately 15 days.

*Time to produce a rooted cutting.*—Approximately 65 days.

*Root description.*—Fibrous, white in color.

*Rooting habit.*—Freely branching.

Plant description:

*Growth habit and general appearance.*—Moderately vigorous, compact-upright growth habit.

*Size.*—Height: Approximately 32.0 cm. Width: Approximately 28.0 cm.

*Branching habit.*—Freely branching, pinching enhances basal branching. Quantity of main lateral branches per plant: Approximately 16.

*Branch.*—Strength: Strong. Length: Approximately 32.0 cm. Diameter: Approximately 2.0 to 4.0 mm. Length of central internode: Approximately 2.0 cm. Texture: Woody. Color of young stems: 183A with venation of 183A. Color of mature stems: N186A with venation of 199D.

Foliage description:

*General description.*—Quantity of leaves per main branch: Approximately 28. Fragrance: none. Form: Simple. Arrangement: Alternate.

*Leaves.*—Shape: Ovate, deeply lobed with three lobes per leaf. Margin: Serrate. Apex of lobes: Acute. Base: Obtuse. Venation pattern: Pinnate. Length of mature leaf: Approximately 5.0 cm. Width of mature leaf: Approximately 4.0 cm. Texture of upper and lower surfaces: Glabrous. Color of upper surface of young foliage: N34A with venation of 150A. Color of lower surface of young foliage: N77A with venation of 150A. Color of upper surface of mature foliage: N186A with venation of 187A. Color of lower surface of mature foliage: 147B with venation of 145B.

*Petiole.*—Length: Approximately 1.4 cm. Diameter: Approximately 1.0 mm. Texture: Glabrous. Color: 183A with venation of 183A.

Flowering description:

*Flowering habit.*—'Minall2' flowers in early to mid-summer.

*Lastingness of individual inflorescence on the plant.*—Approximately two to three weeks.

Inflorescence description:

*General description.*—Type: Corymb, not persistent. Shape: Hemispherical. Aspect: Facing upward and outward. Arrangement: Terminal and axillary. Fragrance: None detected. Quantity per plant: Approximately 72. Diameter: Approximately 3.5 cm. Depth: Approximately 3.0 cm.

*Peduncle.*—Strength: Flexible. Aspect: Erect. Length: Approximately 3.0 mm. Diameter: Approximately 2 mm. Texture: Glabrous. Color: 187B.

Flower description:

*General description.*—Type: Single. Shape: Rotate. Quantity of fully-open flowers per inflorescence: Approximately 36. Appearance: Dull.

*Bud.*—Rate of opening: Generally takes 1 to 2 days for bud to progress from first color to fully-open flower.

*Bud just before opening.*—Shape: Ovoid. Length: Approximately 4.0 mm. Width: Approximately 4.0 mm. Texture: Moderately glandular pubescent. Color: Petal portion 62A, sepal portion 181C.

*Corolla.*—Diameter: Approximately 7.0 mm. Depth: Approximately 4.0 mm.

*Petals.*—Quantity: 5. Shape: Obovate. Margin: Entire. Apex: Obtuse. Base: Attenuate. Length: Approximately 4.0 mm. Width: Approximately 3.0 mm. Texture of upper and lower surfaces: Smooth, glabrous. Color of upper surface when first and fully open: 62C with center of 62B. Color of lower surface when first and fully open: 62D.

*Calyx.*—Diameter: Approximately 2.0 mm. Depth: Approximately 2.0 mm.

*Sepals.*—Quantity per flower: 5. Shape: Subulate. Apex: Acute. Length: Approximately 2.0 mm. Width: Approximately 1.5 mm. Texture of upper (inner) surface: Smooth, glabrous. Texture of lower (outer) surface: Smooth, glabrous. Color of upper (inner) surface: 181C. Color of lower (outer) surface: 181C.

*Pedicel.*—Strength: Strong, flexible. Aspect: Erect to approximately 90° angle. Length: Approximately 8.0 mm. Diameter: Approximately 0.5 mm. Texture: Smooth, glabrous. Color: 181C.

*Reproductive organs.*—Androecium: Stamen quantity: Approximately 25 per flower. Stamen length: Approximately 6.0 mm. Filament length: Approximately 5.0 mm. Filament color: 155B. Anther shape: Oblong, bilobed. Anther length: Approximately 0.5 mm. Anther color: 60A. Pollen amount: Moderate. Pollen color: 155B. Gynoecium: Pistil quantity: 4 per flower. Pistil length: Approximately 5.0 mm. Stigma shape: Globular. Stigma length: Less than 1.0 mm. Stigma color: 158C. Style length: Approximately 3.5 mm. Style color: 155B. Ovary length: Approximately 1.5 mm. Ovary color: 162D.

Seed and fruit production: Neither seed nor fruit production has been observed.

Disease and pest resistance: Resistance to pathogens and pests common to *Physocarpus* has not been observed.

What is claimed is:

1. A new and distinct cultivar of *Physocarpus* plant named 'Minall2', substantially as herein illustrated and described.

* * * * *